United States Patent
Delaney et al.

(10) Patent No.: US 12,094,323 B2
(45) Date of Patent: Sep. 17, 2024

(54) MOBILE COLLECTION OF SENSITIVE INFORMATION INCLUDING TRACKING SYSTEM AND METHOD

(71) Applicants: John Delaney, Ashburn, VA (US); Reed Smith, Leesburg, VA (US); Michael Marino, Glenwood, VA (US)

(72) Inventors: John Delaney, Ashburn, VA (US); Reed Smith, Leesburg, VA (US); Michael Marino, Glenwood, VA (US)

(73) Assignee: Emergency Services Group International Inc., Ashburn, VA (US)

( * ) Notice: Subject to any disclaimer, the term of this patent is extended or adjusted under 35 U.S.C. 154(b) by 0 days.

(21) Appl. No.: 17/831,124

(22) Filed: Jun. 2, 2022

(65) Prior Publication Data
US 2022/0292953 A1 Sep. 15, 2022

Related U.S. Application Data (63) Continuation-in-part of application No. 14/303,064, filed on Jun. 12, 2014, now abandoned.

(60) Provisional application No. 63/233,400, filed on Aug. 16, 2021, provisional application No. 61/834,231, filed on Jun. 12, 2013.

(51) Int. Cl.
*G08B 25/10* (2006.01)
*G06V 40/16* (2022.01)
*G08B 25/01* (2006.01)
*H04W 4/029* (2018.01)

(52) U.S. Cl.
CPC .......... *G08B 25/10* (2013.01); *G06V 40/172* (2022.01); *G08B 25/016* (2013.01); *H04W 4/029* (2018.02)

(58) Field of Classification Search
CPC ...................................................... G08B 25/10
USPC ...................................................... 707/758
See application file for complete search history.

(56) References Cited

U.S. PATENT DOCUMENTS

| | | | | |
|---|---|---|---|---|
| 9,690,538 B1 * | 6/2017 | Doyle, III | ............ | H04W 4/023 |
| 9,980,112 B1 * | 5/2018 | Newby | ................. | H04W 4/021 |
| 10,943,407 B1 * | 3/2021 | Morgan | ................ | G16H 10/60 |
| 2007/0100213 A1 * | 5/2007 | Dossas | ............. | A61B 5/150389 600/509 |
| 2010/0161397 A1 * | 6/2010 | Gauthier | ............ | G01C 21/3605 715/709 |

(Continued)

FOREIGN PATENT DOCUMENTS

| | | | | |
|---|---|---|---|---|
| AU | 2013234381 A1 * | 4/2014 | ............ | G06Q 10/00 |
| AU | 2013201326 A1 * | 9/2014 | | |

*Primary Examiner* — Syling Yen
(74) *Attorney, Agent, or Firm* — Maxwell L. Minch; Maxwell L Minch Esq. PA (57) ABSTRACT

A method of tracking an entity includes generating data relevant to the entity at a first location, storing the data at a server, and accessing at least a portion of the data at the first location or at a second location. The data can include location information, time information, image data, text, and/or biometric data. The data can be encrypted, organized, categorized, updated, accumulated with other data, classified, and/or disseminated, and an automated search can include an image feature recognition and facial recognition search. The entity can be a person, an animal, or an object. A communications system includes a processing device and a server that includes an automated search engine. The server can be configured to perform data analysis, such as data grouping.

14 Claims, 4 Drawing Sheets

(56) References Cited

U.S. PATENT DOCUMENTS

| | | | | |
|---|---|---|---|---|
| 2015/0052062 A1* | 2/2015 | Flomin | ............ | G06Q 30/0633 |
| | | | | 705/26.8 |
| 2015/0332424 A1* | 11/2015 | Kane | .................... | G06F 21/556 |
| | | | | 705/325 |
| 2018/0004898 A9* | 1/2018 | LaBorde | ............. | G06F 21/6245 |
| 2019/0189259 A1* | 6/2019 | Clark | ................ | G16H 10/60 |
| 2021/0319894 A1* | 10/2021 | Sobol | ..................... | G16H 40/67 |
| 2021/0361863 A1* | 11/2021 | Burgess | ............ | A61M 5/16827 |
| 2021/0373676 A1* | 12/2021 | Jorasch | ................ | G06F 3/0383 |

* cited by examiner

MOBILE COLLECTION OF SENSITIVE INFORMATION INCLUDING TRACKING SYSTEM AND METHOD

CROSS-REFERENCES TO RELATED APPLICATION

This invention is a continuation in part of, and claims priority to, co-pending U.S. application Ser. No. 14/303,064 which was filed on Jun. 12, 2014, claiming priority to U.S. Provisional Application No. 61/834,231, which was filed on Jun. 12, 2013. This invention further claims priority to U.S. Provisional Application No. 63/233,400 which was filed on Aug. 16, 2021. The entirety of the foregoing references are incorporated herein by reference.

FIELD OF THE INVENTION

The invention relates to processes and systems used to track people, animals, and objects, and more particularly, tracking people, animals, and objects for review at a remote location different from the location of the people, animals, and objects and the ability to review, analyze, and provide feedback related to the people, animals, and objects at the particular location.

BACKGROUND OF THE INVENTION

There are many situations in which tracking of entities is beneficial, and even necessary. For example, people in a disaster situation are often lost, and how quickly an injured person is located can mean the difference between life and death. As that injured person is moved through the identification-initial treatment-medical care-rehabilitation cycle, it is also beneficial to track the person. However, it is important to track not only the person's location, but also his or her status and treatment history. This is helpful to maximize the patient's results, and also to provide data that can be used to help other similarly-situated patients.

Tracking of livestock is another example in which detailed information, rather than just simple location, is useful, not just for a current situation, but also as an aid to future endeavors. It would be beneficial, for example, to correlate relevant data from other livestock transfers with livestock that are about to be moved, in order to reasonably gauge expectations and to control parameters of the transfer for the best outcome. Tracking of packages, vehicles, and other objects would also be it from the same type of detail and correlation.

Currently, known tracking systems focus on time and location, and do not provide additional details that would be helpful in parallel situations. It would be advantageous to provide a system that tracks entities with more detail, gathers more data and enables simple, powerful data operations to utilize information in current and future undertakings.

BRIEF SUMMARY OF THE INVENTION

According to an aspect of the invention, a method of tracking an entity includes generating data relevant to the entity at a first location, storing the data at a server, and accessing at least a portion of the stored data at the first location or at a second location.

For example, the data can include location information, time information, image data, text, and/or biometric data.

Accessing at least a portion of the data can include decrypting, viewing, manipulating, tracking, sharing, associating, correlating, and/or modifying at least a portion of the data.

The method can also include satisfying an authentication process, prior to accessing at the least a portion of the data. For example, the authentication process can include enrollment in an organizational account.

The method can also include utilizing the data at the server. For example, the data can be encrypted, organized, categorized, updated, accumulated with other data, classified, and/or disseminated. As another example, utilizing the data can include performing an automated search of the data. In this case, the automated search can include an image feature recognition search, which in turn can include a facial recognition search.

Utilizing the data can include performing data analysis, which can include performing data grouping, which in turn can include grouping data sets based on common attributes.

The method can also include accepting additional data from an additional source, which data can be relevant to the entity. The additional data can be identified as being relevant to the entity. Alternatively, the additional data is not identified as being relevant to the entity, and the method includes correlating the additional data with the data to identify the entity.

The method can also include prompting a user for addition data.

The method can also include transmitting the data directly from a first device to a second device, separate from any communication with the server.

The entity can be, for example, a person. In this case, the data can include name, sex, age, height, weight, markings and distinguishing features, address, telephone number, email geolocation, address, medical information, injury information, identification code, and/or family information.

The entity can be, for example, an animal. In this case, the data can include name, sex, age, height, eye color, coat type, length, weight, geolocation, markings and distinguishing features, medical information, injury information, identification code, and/or owner name and contact information.

The entity can be, for example, an object, such as a vehicle or vessel, or a package or container. In this case, the data can include description, size, weight, color, markings, identification code, listing of contents, origin location, destination location, content warnings, handling restrictions, value, and/or insurance information.

According to another aspect of the invention, a storage medium is readable by a processing device and instructions are stored on the medium that, when read by the processing device, cause the method of the invention to be performed by the processing device.

According to another aspect of the invention, a processor includes the storage medium of the invention, a processing device that is communicatively coupled to the storage medium, an input interface configured to receive the generated data, a transmitter configured to send the data to the server, a receiver configured to receive the data from the server, a display that is communicatively coupled to the processing device, and an input/output device that is communicatively coupled to the processing device. The processor also includes a portable housing.

According to another aspect of the invention, a communications system includes the processor of the invention, and the server, such that the processor and the server are mutually communicatively coupled. The processor can be a first processor, and the communications system can also include a second processor that is communicatively coupled with the server and the first processor.

The server can include an automated search engine. For example, the automated search engine can be configured to perform image feature recognition, such as image facial recognition.

The server can be configured to perform data analysis, such as data grouping.

The communications system can also include a data entry terminal that is communicatively coupled to the server. The data entry terminal can include, for example, an input port and a display. The input port can be configured to communicatively couple with a keyboard, a tablet, a computer mouse, a trackball, a stylus, a scanner, a telephone, and/or an image-capture device. The server can be configured to correlate data received from the data entry terminal with data previously stored at the server and/or to associate data received from the data entry terminal with an entity identified at the server.

The server can be configured to encrypt the data, organize the data, categorize the data, update the data, accumulate the data with other data, classify the data, and/or disseminate the data. Organizing the data can include, for example, grouping data sets based on common attributes.

DETAILED DESCRIPTION OF THE INVENTION

Figure 1:
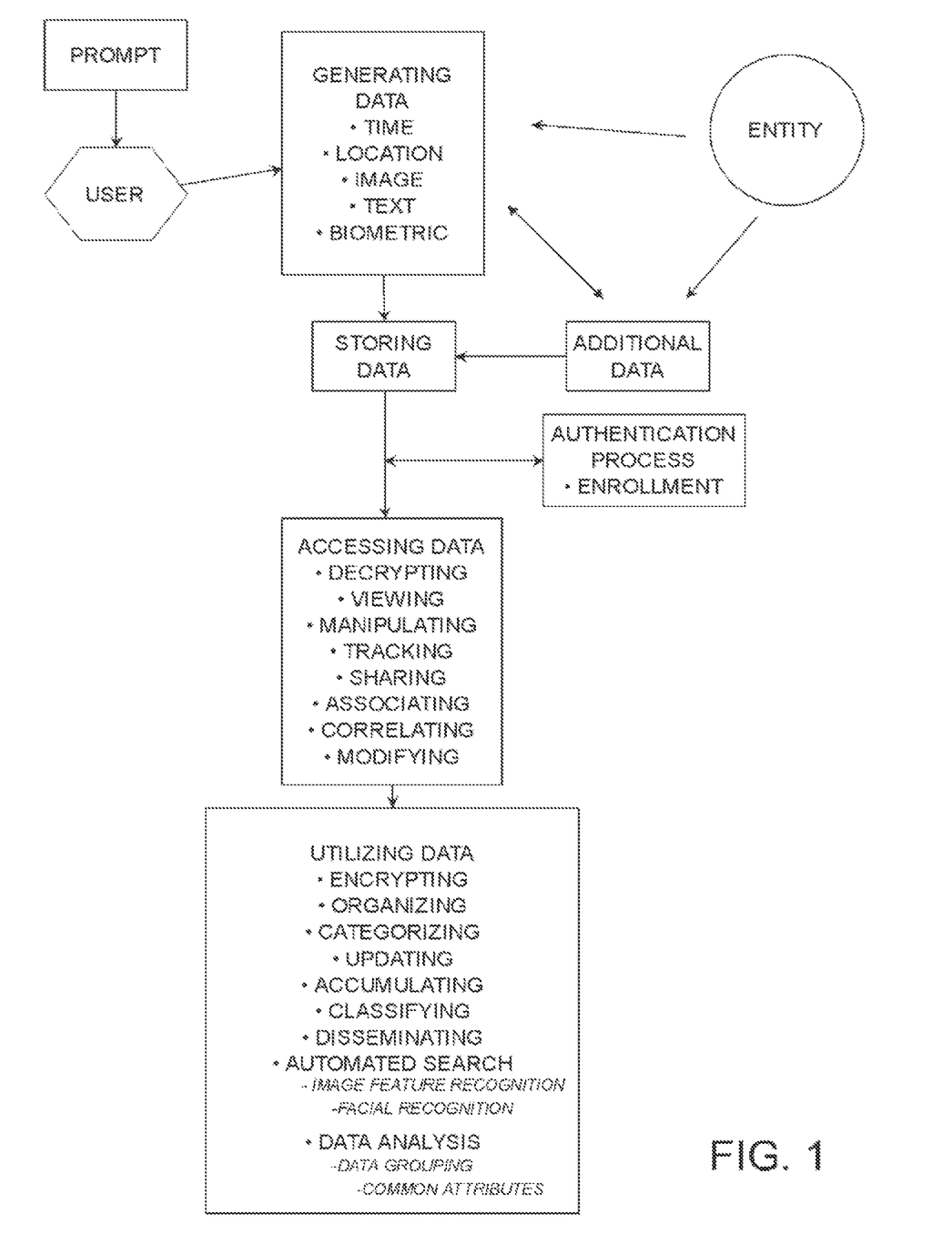
FIG. 1 shows an exemplary process for tracking an entity according to the invention.

As shown in FIG. 1, the method of the invention includes generating data relevant to the entity at a first location. For example, the first location can be a location at which incident has occurred that involves the entity. A user at the location can generate the data, which can include information about the location, such as GPS data, or this data can be generated automatically on actuation of the system. Time data can also be generated automatically or manually by a user. The user can also capture image data of the location and the entity, so as to establish the scene of the incident relevant to the entity, for example. The image data can be a photograph stored as digital file and associated with other data relevant to the entity. The user can also enter text relevant to the entity at the first location. For example, the user can enter text describing the location, the incident, and the entity's involvement in the incident. The text can be entered by any known process, such as by entry via keypad or other alphanumeric text-entry device, via electronic stylus and a tablet, via microphone and text-recognition application, or via scanner and optical character recognition application.

Biometric data can also be generated at the first location. The biometric data can include that which is generated for identification and verification purposes, such as fingerprint data, retinas scan data, and DNA sample data in the case of a human entity. Data indicative of the state of the entity, such as heart rate, respiratory output, and consciousness level, can also be generated.

Once accessed, the data can be utilized in any of a number of ways, subject to a user's authorized rights and restrictions. An authorized user, for example, can encrypt the data to protect against unauthorized access, and/or for authentication purposes. With the proper rights credentials, a user can also organize, categorize, update, classify, and/or disseminate the data, as well as accumulate the data with other data. The objective is to present the data in the most effective way, in order to most effectively track the entity while providing a meaningful chronicle for the entity.

Once arranged, an automated search of the data can be performed to garner particular information related to the entity. For example, key word searching can be performed on the text data, and searching can be performed across data for more than one entity, if authorized, to establish patterns or correlations. The automated search is not limited to text, and can include an image feature recognition search, which in turn can include a facial recognition search. Data analysis, such as data grouping, can also be performed. In this way, data sets can be grouped based on common attributes.

Additional data can be accepted from additional sources, and added to the data stored at the server. When added, the additional data can be identified as being relevant to the entity. Alternatively, the additional data can be provided to the server without being identified as being relevant to the entity. For example, the data can be provided as being interesting in some respect, with the goal of determining if the new data is relevant to an entity already having data stored at the server. The data analysis can be performed on the additional data and compared or correlated with the stored entity data to identify the entity with which it is relevant. The user can be prompted for additional data at any point during the process.

Figure 2:
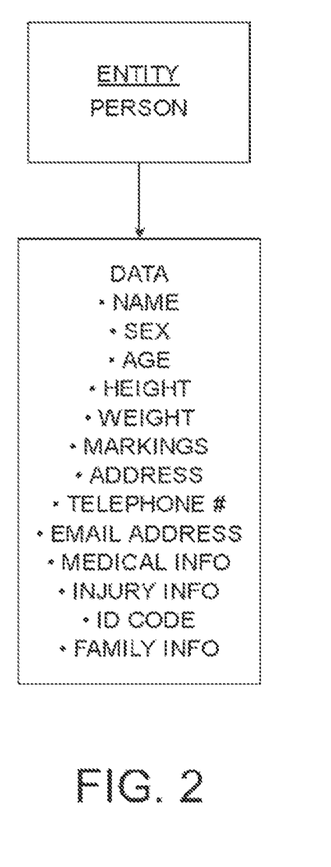
FIG. 2 shows an exemplary embodiment in which the entity is a person.

As shown in FIG. 2, the entity can be, for example, a person. In this case, data relevant to the person, and of interest for future use and reference, can be provided to be stored at the server. For example, the person's name, sex, age, height, weight, markings and distinguishing features, address, telephone number, email address, medical information, geolocation, injury information, identification code, and/or family information can all be provided.

Figure 3:
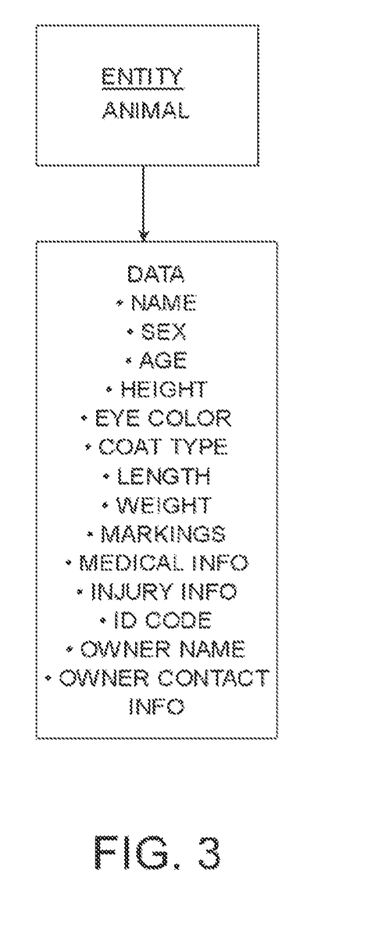
FIG. 3 shows an exemplary embodiment in which the entity is an animal.

Alternatively, the entity can be an animal, such as a pet that is to be tracked, livestock that is to be monitored, or a trap-and-release wild animal that is being studied. In this case, shown in FIG. 3, the data can include name, sex, age, height, eye color, coat type, length, weight, markings and distinguishing features, medical information, injury information, identification code, and/or owner name and contact information.

Figure 4:
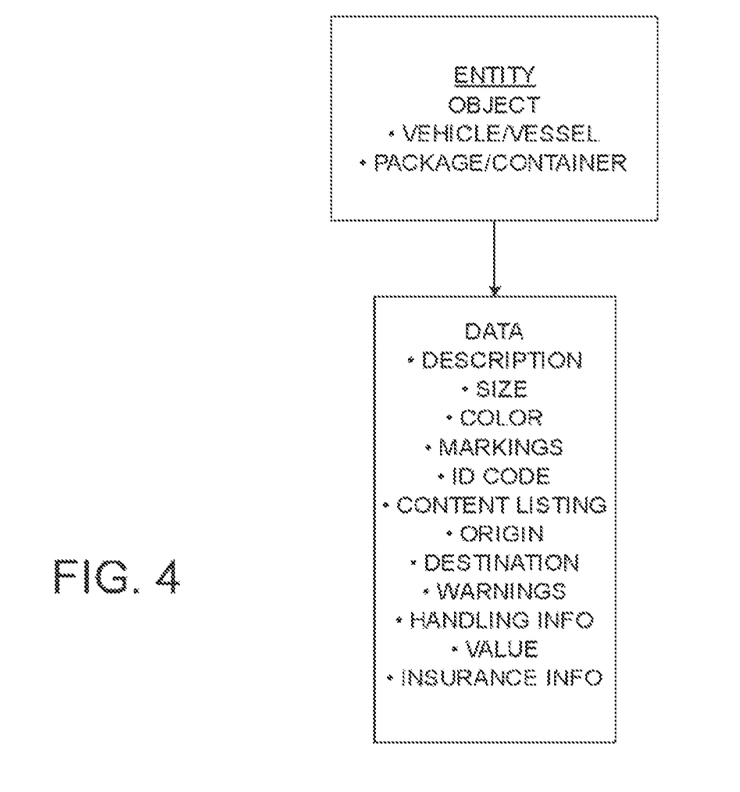
FIG. 4 shows an exemplary embodiment in which the entity is an object.

In addition, the entity can be an object, such as a vehicle or vessel, or a package or container, as shown in FIG. 4. In this case, the data can include description, size, weight, color, markings, identification code, listing of contents, origin location, destination location, content warnings, handling restrictions, value, and/or insurance information. This information is helpful in positively identifying the object, and can be used to track the object as it moves from one location to another. Data entered at each location will assure that the package is monitored effectively and that a history of its movement is documented.

Figure 5:
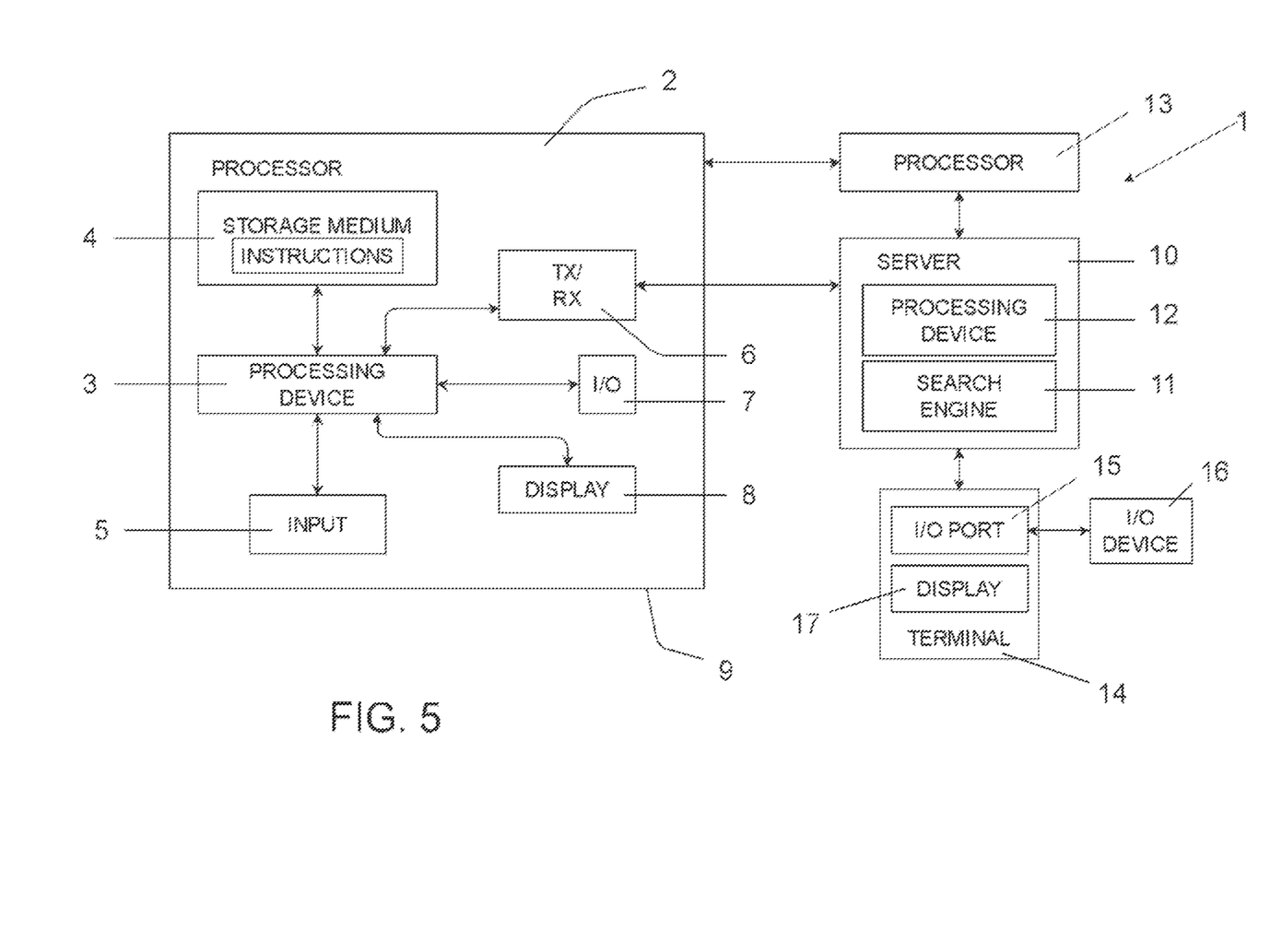
FIG. 5 is a block diagram of an exemplary system according to the invention.

The process of the invention as described above can be put into practice through use of a communications system 1 that includes a processor 2 and a server 10 that are mutually communicatively coupled, as shown in FIG. 5. One or more additional processors 13 can also be communicatively coupled with the server 10 and the first processor 2 as part of the system 1.

The processor 2 preferably includes a storage medium 4, a processing device 3 that is communicatively coupled to the storage medium 4, an input interface 5 configured to receive the generated data, a transmitter 6 configured to send the data to the server 10, a receiver 6 configured to receive the data from the server 10, a display 8 that is communicatively coupled to the processing device 3, and an input/output device 7 that is communicatively coupled to the processing device 3. The processor 2 can be portable, that is, it can also include a portable housing 9. The storage medium 4 is readable by the processing device 3 and stores instructions that, when read by the processing device 3, cause the process of the invention described above to be performed by the processing device 3.

The server 10 can include its own processing device 12 or other device that can function as an automated search engine 11 that can, for example, be configured to perform image feature recognition, such as image facial recognition. The server 10 also can be configured, through the use of a processing device or otherwise, to perform data analysis, such as data grouping.

In certain embodiments, the communications system 1 also includes a data entry terminal 14 that is communicatively coupled to the server 10, configured to provide data to the server 10. The data entry terminal 14 includes an input port 15 that is configured to communicatively couple with an input device 16, such as a keyboard, a tablet, a computer mouse, a trackball, a stylus, a scanner, telephone, and/or an image-capture device. The terminal 14 also includes a display 17. The terminal 14 communicates with the server 10 via a wired connection, or wirelessly according to communications protocols of the type known to or contemplated by those of skill in the art. The server 10 can be configured to correlate data received from the data entry terminal 14 with data previously stored at the server 10 and/or to associate data received from the data entry terminal 14 with an entity identified at the server 10, by means of a server processing device or other means.

Processing functionality at the server 10 also can be configured to encrypt the data, categorize the data, update the data, accumulate the data with other data, classify the data, and/or disseminate the data. The data can also be organized, such as by grouping data sets based on common attributes.

Thus, the system of the invention is a scalable, intuitive, and controlled system that provides the ability to track pets, livestock, people, and objects at various levels of treatment, aid, care, or service during everyday applications, or during tire and emergency medical response (EMS), public health incidents, mass casualty occurrences, small- or large-scale planned events, or any high-volume pre-hospital response, or at any other time that such tracking would be advantageous. Preferably, the system utilizes a handheld application to capture a photograph or other biometric information (such as retina, fingerprint, or DNA information) of the animal, object, or person being tracked and prompts input of pertinent patient/injury/location/destination information by the user. That information is sent to a secured cloud and/or other server, where the information is stored, categorized, and updated repeatedly as needed, and can then be accessed for review, manipulation, or use by others users within the system.

The system is scalable and is contemplated to include any necessary/require storage capacity to allow users to track, categorize, and share any uploaded data. The system has the capacity to collect data from unlimited locations anywhere in the world either through the existing cellular networks, satellite communications networks, hard line connection, or any other communications or data transfer system. Because the system is scalable, it can be utilized to manage data during routine everyday applications or it can be utilized during emergencies, from small-scale incidents up to and including major international disasters and catastrophes.

System Components: Software Application

According to a preferred embodiment, the system utilizes a software application that can be downloaded to any computing platform. For example, the application can be run by a smart phone operating system or other mobile device platform, such as a tablet or optical interface device. Preferably, the basic application can be downloaded and utilized by anyone who registers the software. For advanced-level system operations, additional downloads and advanced operating options can be controlled by the user through access-limited operations that are set up by the user. This includes the ability to set up a personal account as a user on an organizational account. With the organizational access authentication, new users can be added anytime, including during real-time active use at an incident.

The application itself is scalable to hold as many data points as necessary. The application is designed with the ability to capture as much information as is available. At a minimum, the application automatically captures the date and time, the location, and an auto-generated identification code for an incident. These automatic data points are utilized initially to categorize the data into a common 'event' as it is sent to the cloud or server. Other common data points, such as entity identification codes, markings, patient name, triage category, and the like can also be provided for use with the basic application. Preferably in an advanced application, the user can customize in set-up mode to prompt input of any type or amount of information. That data is then sent to the cloud for storage, classification, categorization, and dissemination.

Additionally, in at least one embodiment, the application prompts and allows for the capture of one or several images of the pet, livestock, animal, object, person, or grouping of any such entities. Where used, this image is attached to or otherwise associated with the automatic event data and to the basic or advanced data points as previously listed, and can be used for identification by all permitted users in real time or on review of the data set accessed from the cloud. Iris scans, fingerprint data, facial recognition data, markings recognition data, RFID or barcode readings, DNA, and/or other biometric identifying instances can also be used to associate multiple data points and records on the same subject entered at different times or different locations to reduce subject duplication.

General information for pets, animals, and livestock can include, but is not limited to, name, identification number or code, color(s) of eyes, coat, height, weight, distinguishing features, and owner's information.

General information for people can include, but is not limited to, first, middle, and last names, suffix, sex, age, height, weight, address, country, home phone number, work phone number, cell phone number, email address, parent or guardian name, notes section, and/or other data fields pertinent to the individual incident or needs of the end-user. Additional sections can be added as needed or desired.

During medical emergencies, gathering medical information is critical. This information can include, but is not limited to, chief complaint, priority, blood pressure, pulse, respiration, other vital signs (pulse oximetry, skin color), allergies, medications, history and a notes section. For patients needing ongoing medical care, this initial data collection can be downloaded or copied into existing medical records systems. For large national or international emergency response, it is important to capture family information. All of the information/data, points are menu-driven, manually typed in, or populated via voice recognition.

In at least one embodiment, in the event no connection to a communication network can be made, collected information of a subject or entity remains to be stored on the GPS-capable mobile device and is queued to be sent (and subsequently deleted from the GPS-capable mobile device) upon connection to a communication network. In at least one embodiment, said information stored on the GPS-capable mobile device is not accessible to the user of the mobile-device.

In at least one embodiment, the software application that can be downloaded to one or more GPS-capable mobile device is custom software which provides a user interface on a mobile device for entering information of a subject or entity, whereupon once entry completion of information is selected by a user of the GPS-capable mobile device, the custom software then temporarily stores the information about the subject (including at least one of a name, gender, age, age range, race, ethnicity, height, weight, photograph, biometric data, allergies, address, contact information, clothing, email, physical description, origin, destination, current medical condition, current medical injuries, current medications, hair color, or GPS location of the subject) on the GPS-capable mobile device. It is intended that the information stored on the mobile device cannot be viewed or altered by a user of a GPS-capable mobile device after that information entry completion has been selected by a user. In the presence of a wireless communication network, the temporarily stored information is communicated to the server. Upon completion of communicating the data to one or more wireless communication network, the information is removed or deleted from said one or more GPS-capable mobile device.

Hardware

The system can be used with any handheld device and/or smart phone platform or other operating systems that have yet to be developed that are configured for mobile data collection. For example, a dedicated handheld device is contemplated for use with the system. The application can also be used with any tablet device with a compatible operating system. The data that is stored in the cloud or on a server can be accessed by cell phone, handheld operating system tablet, laptop, desktop computer, or other computer or processing platform by an authorized user.

For communication in areas where a cellular network is not available or has been compromised, the data and application can be accessed using a satellite communication device (SCD) or other device that has been configured with satellite communication capability, or using a handheld device or phone that is configured for communication with an SCD. The handheld device or phone communicates via Bluetooth or other protocol with the SCD to upload and access data to and from the cloud or server.

Certain embodiments of the hardware device also incorporate near-field communication technology that allows the software application to communicate with another software application running on different device by having physical or near-physical contact with the other device. This is effectuated via Wifi, Bluetooth, or other communications protocol deemed appropriate for near-field communication.

Cloud or Server

The system allows for multiple and various devices in divergent locations to upload data and information to a single central, secure server. One or more redundant back-up servers can be provided. This server is access-controlled by the user account whereby users given the appropriate password or other identification and authorization component(s) have limited or unlimited rights to access data and information. The account also allows appropriate use with the appropriate authorization to have total access rights (read and write) to all of the accounts' uploaded data sets. During initial account setup or at a later date with account modifications, the account administrators set up these passwords and user access accounts. Total access rights users can also merge, add, delete, or otherwise modify data set identifiers to identify specific location or additionally categorize or specify on-descript data. Additionally, certain accounts have the option of using their own server for data storage instead of using the cloud server.

Database/Data Mining

In at least one embodiment, the system database correlates data using one or more algorithms to determine if multiple entries in the database refer to a single pet, animal, livestock, object, or patient. For example, one patient may be in the database as a result of data entered by the first responder to arrive on a scene, and the same patient might have a record in the database that was entered by the crew that transported the patient to an emergency room, and the emergency room might also send in a record of the patient once the patient arrives. To maximize the benefit of this system, the system determines common database attributes for all records. When any one record is accessed, a list of possible connected records is developed using feature recognition of photographs (for example, face recognition and other automated grouping algorithms). Additionally, all other information regarding the patient is compared to all records. For example, Patient 1 has a record that indicates he is a middle-aged male, height approximately six feet, with a gunshot wound to the head. In at least one embodiment, the database connects this record to any patients who match a similar description and come from the same incident. Correlations can also be made by a human in the loop. These correlations, along with associated time/place tags, help track the progression of Patient 1 through the various stages of treatment.

As additional records are added to the system database, the data mining algorithms continually update the records to improve the emergency operations center's ability to identify and track patients. As additional information becomes available, such as when family members identify a record, that information can be added to the records and additional correlations can be made.

Patient Tracking User Process

Generally, if the user is working for a fire, police, emergency medical, or emergency management agency, the notification that emergency response is required comes through radio communication. The user may be in a station, in a place of employment, at home, or on the street when the emergency message is dispatched. Upon dispatch, the users, if not committed to another emergency, respond in their respective vehicles to the location provided during dispatch. The number and types of units that are dispatched are predetermined based on the information gathered when the call to 911 or other emergency message was made. Once at the dispatched location, the users investigate to verify the incident location, type, and extent of emergency and determine if additional resources are necessary. If there are individual(s) in need of medical assistance, these patients will be quickly evaluated and prioritized based upon the severity of their injuries; treatment will begin immediately.

In most instances, once the patient is initially assessed at the scene of the incident, the user will take a picture of the injured, affected, or involved individual, add text listing the appropriate information specific to the patient/individual, and upload it via cell signal, Bluetooth, satellite, or other wireless or wired data transfer to the server. If there are numerous patients that require immediate treatment and transport from the scene, a picture of each patient will be the initial priority, as this will capture unique visual identifiers prior to transport of who was at the scene of the incident and directly involved in or affected by the emergency. The users who are transporting the patient(s) to the hospital will at a minimum take and send a picture of the patient to the server, but depending on the time and/or information that is available, can also add any specific identifying information that is available.

Once at the hospital, the users there may take another picture, adding additional pertinent information and sending it to the server. Thus, at each point along the patient's transportation from incident to care, a picture can be taken and information can be added, and the file is sent to the server. This can occur as many times as needed, at as many locations as is necessary, with the picture/information tagged with UPS data to become a virtual breadcrumb trail of where the patient is and has been.

Process for Tracking an Animal or Livestock

The overall process for tracking an animal, pet, or livestock is generally similar to that for humans. A picture of the animal, with or without additional information that is tagged with UPS data, is uploaded to the server at one or more locations as the animal moves from location to location. This process can be used in a variety of setting and incidents, but will generally be initiated during disaster or community/local/regional emergency operations when an animal is lost or unaccounted for. Any individual who has downloaded the application can post a picture, with additional information or a description of the animal, to the server.

This creates a searchable database of lost animals and their locations, as these pictures and information on the animals can be publically posted online to provide owners with the ability to search for and be reunited with their animals. As animals are relocated, a subsequent picture can be taken and sent to the server, or approved users can update the data and information directly in the server or remove the information as it is no longer needed for re-unification purposes.

The lost animal/livestock application can also be used for relocation during normal, non-disaster, or non-emergency times. Users of the application can post pictures and known information of animals that are found to create a lost or misplaced animal database for the public to search. Likewise, animal owners can post descriptions and pictures of their animals when the animals are accounted for, to create a searchable database to be used in the event that an animal goes missing. A user who finds a lost animal that is in the database can enter pertinent information and photos, and the system's server functions can be applied to correlate the entered information with the stored information to identify the animal and get the owner's contact information.

System for Recording and Sharing Information

In at least one embodiment, the present invention provides for a system for recording and sharing information for a particular subject or a plurality of subjects. In such embodiments, the system includes, at least, a wireless communication network, one or more server in communication with the communication network, said server containing a database for compiling information related to one or more subjects, one or more GPS-capable mobile device running custom software, and one or more remote station in communication with said one or more server. In at least one embodiment, the remote station includes a computer having the capability of reviewing the information on the server received from the one or more GPS-capable mobile device.

In at least one embodiment, the information on the server includes the data received from the one or more GPS-capable mobile devices and is stored in one or more database. In at least one embodiment, the information on the server received from the one or more GPS-capable mobile devices is classified in the database by one or more information included. In at least one embodiment, the server is capable of performing one or more of encryption of data communicated by a mobile device, categorize the data communicated by a mobile device, update the data in the database with data communicated by a mobile device, accumulate the data communicated by a mobile device with other data communicated by other mobile devices with custom software, classify the data communicated by a mobile device, disseminate the data communicated by a mobile device, grouping data communicated by a mobile device based on common attributes, or combinations thereof.

In at least one embodiment, one or more remote station connects to the server and is capable of viewing the information stored on the server. The remote station is used to view and assess the received information, to communicate such information to one or more third parties, report information to first responders, report information to emergency or medical personnel, or for racking certain personnel. In at least one embodiment, the remote station is capable of communicating with the specific mobile GPS-enabled device that captured the information of one or more subjects.

In at least one embodiment, the information on the server received from the one or more GPS-capable mobile devices is populated into a graphical user interface and viewed on said remote station computer. In at least one embodiment, the information on the server received from the one or more GPS-capable mobile devices is geo-located on a map at one or more remote station.

Sentiment Analysis and Pain Scoring

In at least one embodiment, the system includes software which further performs sentiment analysis and pain scoring of one or more subjects where facial imaging information is available. Where used, first a sentiment analysis of said images of one or more subject is performed by analyzing facial features of the subject from the images captured by one or more of the GPS-capable mobile devices and comparing the facial features against a database of facial features to identify the sentiment of the subject at the time the image was captured. The resulting analysis broadly classifies the image into fractional-associated sentiments. For example, an analysis may reveal both surprise and anger and negatively correlate any emotions of joy or humor.

In at least one embodiment, once the sentiment analysis is completed, the sentiment is compared to a database of pain scores associated with one or more identified sentiment. Upon successful matching of a sentiment analysis, the corresponding pain score is assigned to the subject and stored in the database along with the other information stored regarding said subject. In at least one embodiment, the pain score is calculated by first evaluating the percentage of emotion generated by the sentiment analysis, comparing the percentage of emotion with a database relating one or more percentage of emotion or range of percentage of emotion with pain data, and assessing a pain score for the subject. It should be appreciated that providing an objective pain score measure is helpful to medical responders. The pain score allows for medical responders to prioritize those patients in need, indicate those patients who need for advanced care to deliver pain management, or simply indicate that an injury exists for a patient that needs to be assessed.

Homeless Tracking

In at least one embodiment, the inventive method is used for the tracking of homeless persons. In such embodiments, the remote station in communication with the one communication network includes one or more computing devices running custom homeless tracking software. In such embodiments, the remote station receives the information obtained from the one or more mobile devices pertaining to a homeless person, tracks the GPS location of the data received along with any other information sent relating to that person from the one or more mobile device. It is intended that the data received would be updated over time, thus allowing tracking movements and health conditions of homeless persons who remain or are routinely homeless. Accordingly, the system will store the information related to the homeless individual in the database stored on the server, or update existing information for that particular homeless individual.

Responding to Mass Casualties

In at least one embodiment, the inventive method is used for the tracking injured persons who are part of a mass casualty scenario. In such embodiments, the remote station in communication with the one communication network includes one or more computing devices running custom injury tracking software. In such embodiments, the remote station receives the information obtained from the one or more mobile devices pertaining to a one or more injured person at the scene of a mass casualty scene. Injury data, GPS location, and pictures of wounds and the injured persons are received by the remote station from the server along with any other information sent relating to that injured person from the one or more mobile devices. The remote station is operable by one or more medical personnel or other personnel qualified for assessing injury and severity. Upon the finding by the medical personnel that one or more injured persons requires immediate medical attention, medical personnel are alerted and provided information, such as CRS location, injury description and injury diagnosis by the remote medical personnel, and alerting medical personnel. In at least one embodiment, medical personnel have one or more mobile device running custom injury tracking software, where medical personnel are alerted based on their proximity to the injured subject that the remote station has elevated the need for medical response.

Other Uses

The system can be used in other scenarios, and for tracking other types of items. For example, it can be used in shipping to track shipping vehicles, containers, crates, and even individual packages. Moving vans can similarly be tracked, as can families traveling on vacation or executives traveling for business, or produce shipped from farm to table. In any instance where there is loss of life, to include disasters where there is a large loss of life, the system can be utilized as a fatality management tool which will aid in identifying the location, description, and number of dead, as well as their continued tracking. The system can be utilized as a means of remote identification of deceased personnel through the use of facial recognition capability or the ability to capture pictures, biometric, other relevant information specific to the individual such as birth marks, tattoos, distinguishing features, and the like by persons either on- or off-site in a secure fashion.

The system can also be used as the initial documentation for patient care reports for both pre-hospital and in-hospital patients. Accordingly, the system may be the means by which the patient, whether pre-hospital or in-hospital, is linked with a paper-based care report or electronic patient care report (ePRC). Application of the system in this area connects the patient via biometric or other entered identifiers from the system to the patient care report as directed by the healthcare provider. As patients are transferred between providers or facilities, the system links patient information by utilizing the patient's intrinsic information or biometric data as the identifier for the chart or patient information which is stored in on electronic format in a central electronic database. This process is repeated when the patient arrives at the new facility or contacts a new healthcare provider and is matched via the system to his/her/its specific information. In the healthcare application, the system will do this in a secure fashion by which patient information is protected according to applicable laws and healthcare regulations.

Additionally, the system can be used for counting and tracking of homeless persons in a geographic area. The system can also be used by countries, organizations, or other entities to pre-identify and categorize individuals prior to a disaster for the purposes of post-disaster identification and prioritization of aid and resources. An organization may pre-populate the system database prior to initiation of some planned or unplanned event for the expressed purpose of organizing systems or processes after a manmade or natural disaster has occurred. This is accomplished by capturing identifying information within the system via means mentioned above (entered, voice command, biometric, etc.) into a handheld, mobile device or through an optical instrument. The system then uploads information to a centralized database which is then manipulated as described above for the purposes of various applications of tracking persons displaced or involved in an incident, indicating the transitory nature of a population after an incident, provide situational awareness location of personnel pre- or post-event, identify affected personnel for means of remuneration or aid dispersal, or other applications whereas tracking of personnel for humanitarian or disaster relief may be beneficial.

Those of skill in the art will recognize that use of the application can be expanded to any scenario in which a person, animal, vegetation, or object is moved from place to place and advantageously tracked from origin to destination.

Particular exemplary embodiments of the present invention have been described in detail. These exemplary embodiments are illustrative of the inventive concept recited in the appended claims, and are not limiting of the scope or spirit of the present invention as contemplated by the inventors.

The invention claimed is:

1. A system for recording and sharing information for a particular subject or a plurality of subjects, the system comprising:
   a wireless communication network;
   one or more server in communication with the communication network, said server containing a database of compiled information related to one or more subjects;
   one or more GPS-capable mobile device running custom software, the custom software performing the method of:

providing a user interface on said GPS-capable mobile device for entering information of said subject;

capturing one or more facial image information and GPS location information of one or more subject with said GPS-capable mobile device and storing said one or more facial image and GPS location;

performing a sentiment analysis of said one or more facial image including analyzing facial features of said subject from said one or more facial image and comparing said facial features against a database of facial features to identify the sentiment of the subject at the time the one or more facial image was captured;

relating sentiment analysis to a pain score;

storing said pain score along with the information and said one or more facial image of said subject;

storing additional information about said one or more subject said information including at least one of a name, gender, age, age range, race, ethnicity, height, weight, photograph, biometric data, allergies, address, contact information, clothing, email, physical description, origin, destination, current medical condition, current medical injuries, current medications, or hair color of the subject;

communicating said information and said additional information to said server; and removing said information and additional information from said one or more GPS-capable mobile device upon communication of said information to the wireless network;

one or more remote station in communication with said one or more server, the remote station comprising a computer having the capability of reviewing said information on the server received from the one or more GPS-capable mobile device, entered into one or more database, geo-located on a map, classified in the database by one or more information included, and populated into a graphical user interface and viewed on said remote station computer.

2. The system of claim 1 wherein performing a sentiment analysis of said images further performs the method of:
analyzing facial features of said subject from said one or more facial image; and
comparing said facial features against a database of facial features to identify the sentiment of the subject at the time said one or more facial image was captured.

3. The system of claim 1 wherein relating sentiment analysis to a pain score further performs the method of:
evaluating the percentage of emotion generated by said sentiment analysis;
comparing the percentage of emotion with a database relating one or more percentage of emotion or range of percentage of emotion with pain data; and
assessing a pain score for said subject.

4. The system of claim 1 wherein the method performed by the custom software further comprises that in the event no connection to a wireless communication network, the information waits to be sent, but is not accessible to the user of the mobile-device.

5. The system of claim 1 wherein the remote station uses said information from a subject or a plurality of subjects to locate a subject at or around is located within the system, to communicate such information to a third party, report information to first responders, report information to emergency or medical personnel, tracking certain personnel.

6. The system of claim 1 wherein the remote station is capable of communicating with the specific mobile GPS-enabled device that captured the information of one or more subjects.

7. The system of claim 1 wherein said biometric data is one or more of fingerprint data, retinas scan data, heart rate, respiratory output, and consciousness level, DNA sample data, or combinations thereof.

8. The system of claim 1 wherein said server performs one or more of encryption of data communicated by a mobile device, categorize the data communicated by a mobile device, update the data in the database with data communicated by a mobile device, accumulate the data communicated by a mobile device with other data communicated by other mobile devices with custom software, classify the data communicated by a mobile device, disseminate the data communicated by a mobile device, grouping data communicated by a mobile device based on common attributes, or combinations thereof.

9. The system of claim 1 wherein said information is entered into the database by the server grouping such information by the facial recognition information, the pain score of the subject, the GPS location of the subject, or combinations thereof.

10. The system of claim 1 wherein said user of said GPS-enabled mobile device is contacted by said remote station upon the receipt of a high pain score, identification of an emergency condition relating to, caused by, or occurring to a subject by the remote station, or combinations thereof.

11. A system for recording and sharing information for a particular subject or a plurality of subjects, the system comprising:
a wireless communication network;
one or more server in communication with the communication network, said server containing a database of compiled information related to one or more subjects;
one or more GPS-capable mobile device running custom software, the custom software performing the method of:
providing a user interface on said GPS-capable mobile device for entering information of said subject;
capturing one or more facial image information and GPS location information of one or more subject with said GPS-capable mobile device and storing said one or more facial image and GPS location;
performing a sentiment analysis of said one or more facial image including analyzing facial features of said subject from said one or more facial image analyzing facial features of said subject from said one or more facial image by comparing said facial features against a database of facial features to identify the sentiment of the subject at the time said one or more facial image was captured, and comparing said facial features against a database of facial features to identify the sentiment of the subject at the time said one or more facial image was captured;
relating sentiment analysis to a pain score;
storing said pain score along with the information and facial image of said subject;
storing additional information about said one or more subject said information including at least one of a name, gender, age, age range, race, ethnicity, height, weight, photograph, biometric data, allergies, address, contact information, clothing, email, physical description, origin, destination, current medical condition, current medical injuries, current medications, or hair color of the subject;
communicating said information and said additional information to said server; and
removing said information and additional information from said one or more GPS-capable mobile device upon communication of said information to the wireless network;
one or more remote station in communication with said one or more server, the remote station comprising a computer having the capability of reviewing said information on the server received from the one or more GPS-capable mobile device, entered into one or more database, geo-located on a map, classified in the database by one or more information included, and populated into a graphical user interface and viewed on said remote station computer.

12. The system of claim 11 wherein relating sentiment analysis to a pain score further performs the method of:
evaluating the percentage of emotion generated by said sentiment analysis;
comparing the percentage of emotion with a database relating one or more percentage of emotion or range of percentage of emotion with pain data; and
assessing a pain score for said subject.

13. A system for recording and sharing information for a particular subject or a plurality of subjects, the system comprising:
a wireless communication network;
one or more server in communication with the communication network, said server containing a database of compiled information related to one or more subjects;
one or more GPS-capable mobile device running custom software, the custom software performing the method of:
providing a user interface on said GPS-capable mobile device for entering information of said subject;
capturing one or more facial image information and GPS location information of one or more subject with said GPS-capable mobile device and storing said one or more facial image and GPS location;
performing a sentiment analysis of said one or more facial image including analyzing facial features of said subject from said one or more facial image analyzing facial features of said subject from said one or more facial image;
relating sentiment analysis to a pain score by evaluating the percentage of emotion generated by said sentiment analysis, comparing the percentage of emotion with a database relating one or more percentage of emotion or range of percentage of emotion with pain data, and assessing a pain score for said subject;
storing said pain score along with the information and facial image of said subject;
storing additional information about said one or more subject said information including at least one of a name, gender, age, age range, race, ethnicity, height, weight, photograph, biometric data, allergies, address, contact information, clothing, email, physical description, origin, destination, current medical condition, current medical injuries, current medications, or hair color of the subject;
communicating said information and said additional information to said server; and
removing said information and additional information from said one or more GPS-capable mobile device upon communication of said information to the wireless network;
one or more remote station in communication with said one or more server, the remote station comprising a computer having the capability of reviewing said information on the server received from the one or more GPS-capable mobile device, entered into one or more database, geo-located on a map, classified in the database by one or more information included, and populated into a graphical user interface and viewed on said remote station computer.

14. The system of claim 13 wherein performing a sentiment analysis of said images further performs the method of:
analyzing facial features of said subject from said one or more facial image; and
comparing said facial features against a database of facial features to identify the sentiment of the subject at the time said one or more facial image was captured.

\* \* \* \* \*